United States Patent [19]

Fuertes et al.

[11] Patent Number: 4,985,553

[45] Date of Patent: * Jan. 15, 1991

[54] PROCESS FOR THE OXIDATION OF DI-, TRI-, OLIGO- AND POLYSACCHARIDES INTO POLYHYDROXYCARBOXYLIC ACIDS, CATALYST USED AND PRODUCTS THUS OBTAINED

[75] Inventors: Patrick M. Fuertes, Lillie; Guy M. Fleche, Merville, both of France

[73] Assignee: Roquette Freres, Lestrem, France

[*] Notice: The portion of the term of this patent subsequent to Jun. 27, 2006 has been disclaimed.

[21] Appl. No.: 7,654

[22] Filed: Jan. 28, 1987

[30] Foreign Application Priority Data

Jan. 30, 1986 [FR] France ................ 86 01305

[51] Int. Cl.$^5$ .................. C08B 31/00; C08B 37/00; C13K 1/00; C07H 1/00; C07C 51/00
[52] U.S. Cl. ........................ 536/124; 536/105; 536/128; 536/110; 536/119
[58] Field of Search ........... 536/124, 105, 128, 110, 536/119

[56] References Cited

U.S. PATENT DOCUMENTS

| | | | |
|---|---|---|---|
| 3,450,692 | 6/1969 | Hyldon et al. | 536/105 |
| 3,553,193 | 1/1971 | Le Roy et al. | 536/105 |
| 3,557,084 | 1/1971 | Hyldon et al. | 536/105 |
| 3,615,786 | 10/1971 | Moskaluk | 536/105 |
| 3,665,000 | 5/1972 | Hills | 536/105 |
| 3,873,614 | 3/1975 | Lamberti et al. | 536/105 |
| 4,040,862 | 8/1977 | Voigt et al. | 536/105 |
| 4,048,434 | 9/1977 | Speakman | 536/105 |
| 4,845,208 | 7/1989 | Fuertes et al. | 536/124 |

FOREIGN PATENT DOCUMENTS

| | | |
|---|---|---|
| 0142725 | 5/1985 | European Pat. Off. |
| 0151498 | 8/1985 | European Pat. Off. |
| 2075502A | 11/1981 | United Kingdom |

OTHER PUBLICATIONS

"Chemical Abstracts", vol. 103, 1985, p. 638, Abstract No. 88175q, Columbus, Ohio.
"Chemical Abstracts", vol. 102, 1985, Abstract No. 149721t Columbus, Ohio.
"Chemical Abstracts", vol. 83, 1975, p. 539, Abstract No. 43639w, Columbus, Ohio.

*Primary Examiner*—Ronald W. Griffin
*Assistant Examiner*—Everett White
*Attorney, Agent, or Firm*—Larson and Taylor

[57] ABSTRACT

Process for the selective oxidation of di-, tri-, oligo- and polysaccharides comprising a reducing terminal function of the aldose type into polyhydroxycarboxylic acids, wherein the oxidation is carried out in an alkaline medium by means of an oxygen-containing gas, in the presence of a noble metal based catalyst selected from the group constituted by palladium, platinum, rhodium and osmium and fixed on an inert support, said catalyst being "doped" with one or several metals, or promoters, of Groups IV, V or VI of the Periodic Table.

26 Claims, No Drawings

PROCESS FOR THE OXIDATION OF DI-, TRI-, OLIGO- AND POLYSACCHARIDES INTO POLYHYDROXYCARBOXYLIC ACIDS, CATALYST USED AND PRODUCTS THUS OBTAINED

This invention essentially relates to a process for the oxidation of di-, tri-, oligo- and polysaccharides into polyhydroxycarboxylic acids.

It is known to prepare polyhydroxycarboxylic acids by oxidizing the corresponding polysaccharides using electrochemical techniques in the presence of $CaBr_2$; it has also been proposed to oxidize the free aldehyde functions of the polysaccharides with sodium hypobromite or hypochlorite; finally, the catalytic oxidation of said polysaccharides has been proposed.

The aforesaid electrochemical processes, besides being complex, entail many drawbacks, especially as regards the purification of the products thus obtained and the removal of bromine following the oxidation reaction. They therefore, do not prove economically profitable on an industrial scale.

The techniques of oxidation of the free aldehyde functions by means of Na-hypobromite or hypochlorite are not selective and, actually, bring about breakage of the glucosidic bonds along with a generation of oxidized products having a low molecular mass.

Catalytic oxidation using palladium or platinum based catalysts, fixed on carbon has been disclosed in French patent No. 70 18091. These processes lack selectivity and not only lead to low conversion rates, but furthermore, do not make it possible to avoid over-oxidation phenomena, especially in the case of platinum.

The main purpose of the present invention therefore is to remedy these drawbacks and to provide a process for the selective oxidation of the polysaccharides, thereby better meeting the various prerequisites of the practice in comparison to the methods already available.

Now, Applicants have found that, surprisingly and unexpectedly, it was possible, in an alkaline medium, to selectively oxidize under advantageous economical conditions, the terminal aldehyde functions of the polysaccharides into carboxylic functions, without any degradation of the initial polymeric structure and without the occurrence of any secondary reaction associated with the disruption of the glucosidic bonds, when using catalysts based on noble metals of the group consisting of palladium, platinum, rhodium and osmium, fixed on an inert support and "doped" with one or several of the metals of Groups VI, V or VI of the Periodic Table or system, which constitute the "promoters".

Consequently, the process according to the invention for the preparation of polyhydroxycarboxylic acids is essentially characterized by the fact that there are oxidized one or several polysaccharides in an alkaline medium and, by means of an oxygen-containing gas, in the presence of a catalyst based on a noble metal of the group consisting of palladium, platinum, rhodium and osmium, fixed on an inert support and "doped" with one or several of the metals of Groups IV, V or VI of the Periodic Table or system.

In addition to this process of preparation of polyhydroxycarboxylic acids, another object of the invention is use of the aforesaid catalysts in connection with their application to said process as well as the polyhydroxycarboxylic acids obtained by using same.

The polysaccharides, whose selective oxidation is made possible by means of the process in accordance with the invention comprise:

disaccharides having a reducing function of the aldose type such as lactose, maltose, isomaltose, cellobiose, xylobiose and mannobiose, as well as trisaccharides, oligosaccharides and products resulting from the hydrolysis of starch cellulose and hemicelluloses containing a reducing terminal function of the aldose type and a mixture of these polysaccharides.

The starch hydrolysis is generally carried out by the acid and/or enzymatic way and leads to the production of glucose syrups. Among products from the hydrolysis of hemicelluloses, there may be mentioned the D-galacto-D-mannans, the D-gluco-D-mannans, the L-arabino-D-xylans, and the D-xylo-L-arabinans.

The molecular mass of the polysaccharides does not constitute a limitation to the invention, provided of course that the products to be oxidized are water-soluble. However, the polysaccharides with a high molecular mass have high viscosities in aqueous solution, so that it becomes necessary to proceed with low concentrations, which does not prove commercially advantageous.

In the case of use of the process in accordance with the invention in the oxidation of products resulting from the starch hydrolysis, the mixture of polysaccharides resulting from the hydrolysis is characterized by its reducing power or D.E. (dextrose-equivalent) and by the glucidic distribution or spectrum; the process according to the invention can be carried out on any starch hydrolysate or glucose syrup whose DE is comprised between 90 and 5 and, preferably, between 85 and 15 and, still more preferably, between 75 and 15.

The lower limit of the DE is imposed, on the one hand, by viscosity and solubility problems as mentioned above, and, on the other hand, by the kinetic which decreases rapidly decreasing with the degree of polymerization or DP.

The catalysts based on noble metal, especially those based on palladium and/or platinum, are known per se; the "support" generally consists of finely divided carbon, alumina, silica, barium sulfate or titanium oxide; carbon on the one hand, and Pd and Pt on the other hand, being preferred.

The Applicants have found out that, surprisingly, the presence in these catalysts of one or several of the aforesaid promoters makes it possible to decisively increase the kinetic, yield and selectivity of the oxidation reactions, in an alkaline medium, of the polysaccharides into polyhydroxycarboxylic acids.

The incorporation of the aforesaid promoters into the catalyst can be carried out before or after having deposited the noble metal onto the inert support or simultaneously with this depositing operation.

It is also possible to introduce the promoter in solution into a reaction medium containing the polysaccharides in aqueous solution as well as a catalyst based on noble metal. In this case, the deposit of the promoter is performed in situ in the reaction medium.

Preferably, the promoters are used in the form of salts in order to facilitate their solubilization in an aqueous, generally acid medium.

For the preparation of the "doped" catalyst, the solution of the promoter salts is mixed with an aqueous suspension of the catalyst consisting of the noble metal, the impregnation of said catalyst with the promoter in the form of salt being effected by maintaining the mixture under stirring for a duration of at least a few seconds to several hours, generally between 15 minutes and 2 hours.

The suspension thus impregnated with the supported catalyst based on noble metal is then made alkaline by adding a base such as NaOH, KOH, sodium carbonate and other, before the completion of the step of reduction of the promoter which can be performed at a temperature between 20° C. and 100° C. by means of chemical reducing agents such as formalin, sodium formate, sodium boron hydride, hypophosphorous acid, hydrazine, glucose or other reducing sugars.

The catalyst thus reduced is filtered, washed, dried or used as such.

It should be pointed out that the reduction of the catalyst can be performed within the reaction medium of the catalytic oxidation process since the latter initially takes place in the presence of reducing polysaccharides and in an alkaline medium.

Preferably, a catalyst obtained by the addition of the promoter subsequently to the noble metal deposit onto the inert support is used; the promoter can also be incorporated into a commercially available catalyst based on noble metals on an inert support.

The content of promoters in the final catalyst, expressed in terms of metal, is generally comprised between 1 and 300 wt % with respect to the noble metal.

Still preferably, as promoter, bismuth, lead, antimony, tin or selenium and, most particularly preferred, bismuth and lead are used.

Consequently, the catalysts preferred in connection with the process according to the present invention are those obtained by depositing bismuth and/or lead onto a catalyst based on palladium and/or platinum, supported on carbon.

The palladium and/or platinum content expressed in terms of metal is generally comprised between 1 and 10 wt % with respect to the support.

The bismuth and/or lead content expressed in terms of metal is comprised between 1 and 300 wt % with respect to palladium and/or platinum, preferably between 5 and 100%.

This being said, the process in accordance with this invention for the preparation of polyhydroxycarboxylic acids and of their salts comprises:

the introduction of an aqueous solution of at least one polysaccharide into a reaction vessel equipped with a stirring device, said solution preferably having a concentration of polysaccharides preferably comprised between 5 and 60 wt %, the lower limit being imposed by a concern for profitability and the upper limit by the solubility of oxygen in highly viscous media, and the risk of crystallization of the salts of aldonic acids formed during the reaction, the oxidation of a glucose syrup being, for example, preferably performed at a concentration comprised between 20 and 40 wt %, the dispersion into this solution of the catalyst used according to the invention, the quantity of catalyst introduced being such that the quantity of palladium and/or platinum, expressed in terms of metal, is comprised between 0.005 and 1 wt % with respect to the polysaccharides and, preferably, between 0.01 and 0.4%, the starting of the reaction by the simultaneous supply of a flow of air or oxygen-containing gas and of an alkaline agent, the reaction temperature generally ranging between 20° and 90° C., preferably between 25° and 60° C. for a reaction time comprised between 30 minutes and 5 hours, the introduction into the reaction medium of alkaline agents with a view to neutralizing the polyhydroxycarboxylic acids formed, in order to maintain a constant catalytic activity during the reaction and, more precisely, in order to keep the pH of the reaction medium at a value sufficient to ensure the desorption of the polyhydroxycarboxylic acids formed and to avoid the over-oxidation of same, without however, having this pH reaching values likely to promote reactions of isomerization of aldose into ketose, said pH being maintained in the practice at a value comprised between 7.5 and 11.0, preferably between 8.0 and 10.0.

The alkaline agent is selected from the group comprising sodium hydroxide, potassium hydroxide, calcium hydroxide, lithium hydroxide, magnesium hydroxide, depending on the goal to be reached; thus, sodium hydroxyde will be used in order to obtain sodium salt from the polyhydroxycarboxylic acid corresponding to the polysaccharide used; zinc or manganese carbonate can also be used as well as any other zinc or manganese salts for which the corresponding hydroxides are obtained in situ by adding an alkaline agent such as sodium hydroxide or potassium hydroxide.

The catalysts used according to the invention and obtained by depositing a promoter, particularly the palladium-bismuth or palladium-lead catalysts, supported on carbon, have a catalytic activity which is practically independent from the degree of polymerization of the polysaccharides subjected to oxidation, so that the speed of reaction remains practically constant when mixtures of polysaccharides such as products resulting from the starch hydrolysis are oxidized; in such a case, no reaction of over-oxidation or degradation of the polysaccharides is observed.

The rate of conversion of the polysaccharides subjected to the process according to the invention is higher than 90% and more particularly comprised between 95 and 100%.

These remarkable performances are all the more exceptional since they are preserved even in the case of an important number of recyclings of the catalysts used in accordance with the invention.

The catalysts which are preferably used, i.e. those wherein the promoter is deposited after having deposited the noble metal onto the support are easily prepared and show a high stability and can be subjected to regeneration by depositing a new promoter charge, the required quantity of promoter being, anyhow, always low since the deposit is exclusively carried out on the surface of the noble metal.

The oxidized polysaccharides, obtained by use of the process according to the invention can be used in many fields, especially in sodium salt form, as chelating or complexing agents, for the cleaning of glass or metal articles or items, especially of iron or aluminum, as additives for detergents, or in the field of hydraulic binders as a fluidifying agent reducing water, as concrete retarding admixtures, etc.

They can also be used in the pharmaceutical field, as for example, calcium lactobionate.

The invention will be best understood by means of the following non-limiting examples which describe among other things advantageous embodiments of the invention.

There is first cited a few examples for the preparation of the catalyst used in the process according to the invention.

EXAMPLE 1

Preparation of a catalyst containing 5% of Pd and 3.5% of Bi on carbon, by depositing bismuth onto a palladium on carbon or Pd/C catalyst commercially available.

A quantity of 6 g of dry Pd/C catalyst commercially available (DEGUSSA 198 R/W with 5% Pd) is suspended in 80 ml of distilled water acidified with 1 ml of concentrated hydrochloric acid (37% HCl). To this suspension, there is added a solution consisting of 0.3 g of bismuth subnitrate dissolved in a mixture of 2 ml of concentrated hydrochloric acid and 5 ml of distilled water.

After stirring for two hours, there are introduced 4 g of caustic sodium hydroxide in solution in 30 ml water. The mixture is brought to a temperature of 40°–50° C. for 4 hours, then 1.5 ml of formalin (37–38% aqueous solution) is added. The mixture is brought to 85° C. for 1 hour. The catalyst thus obtained is filtered and washed.

EXAMPLE 2

Preparation of a catalyst containing 5% of Pd and 3.5% of Bi on carbon by depositing bismuth prior to depositing palladium.

A quantity of 6 g of dry active carbon is suspended in 80 ml of distilled water. To this suspension, there is added a solution consisting of 0.3 g of bismuth subnitrate dissolved in a mixture of 3 ml of concentrated hydrochloric acid and 5 ml of distilled water.

Stirring is continued for 6 hours in order to have the bismuth completely adsorbed on the active carbon. Then, a solution of 0.5 g of palladium chloride (0.3 g of metal palladium) in 1.5 ml of hydrochloric acid and 5 ml of distilled water is added. 4 g of caustic NaOH in solution in 30 ml of water are added and the mixture is brought to a temperature of 40° C. for 5 hours. After having added 1.5 ml of a 37% formalin solution, the suspension is maintained at 85° C. for one hour. The catalyst thus obtained is filtered and washed.

EXAMPLE 3

Preparation of a catalyst containing 5% of Pd and 2.5% of Pb on carbon by depositing the lead onto a Pd/C catalyst commercially available.

A quantity of 6 g of dry Pd/C catalyst commercially available (DEGUSSA 198 R/W with 5% Pd) is suspended in 80 ml of distilled water. To this suspension, 20 ml of an aqueous solution containing 0.3 g of lead acetate are added. The lead is caused to be absorbed for one hour under stirring. 30 ml of an aqueous solution containing 4 g of $Na_2CO_3$ are added and the mixture obtained is brought to a temperature at 40° C. for four hours. 1.5 ml of formalin is added and the suspension is maintained at 85° C. for 1 hour. The catalyst thus obtained is then filtered and washed with distilled water.

There is now described a few examples of the use of the process according to this invention.

EXAMPLE 4

Preparation of sodium maltobionate by oxidation of maltose.

Four experiments are carried out by introducing each time individually into a reaction vessel having a capacity of 1 l, equipped with a stirring device and a thermometer, a sintered rod for the blowing of air, an electrode and a continuous introduction device, a quantity of 666 g of an aqueous maltose solution with 30% of solid matters as well as a quantity of 6 g of respectively each of the dry catalysts according to examples 1 to 3 for the first three experiments (experiments a, b and c) and a quantity of 6 g of the dry catalyst commercially available, used in examples 1 and 3 for the fourth experiment (experiment d).

The reaction is effected at 35° C. and air is blown while simultaneously introducing a 30% aqueous solution of NaOH in order to maintain the pH at a value of 9.0±0.5.

The reaction is stopped when the theoretical quantity of sodium hydroxide has been consumed, which gives the reaction speed; the reaction product is then separated by filtration and the percentage of residual reducing sugars is determined, which makes it possible to calculate the rate of conversion of the substrate or feedstock.

The maltose used in experiment c is a maltose having a purity of 99.9% and the one used in the experiments a, b and d has 95% purity.

In table I are recorded the results from the abovementioned measurements and determinations.

TABLE I

| Experiment Nr | Catalyst used | Reaction time (hr) | Reducing sugars (%) | Maltose conversion rate (%) |
|---|---|---|---|---|
| a | 5% Pd and 3.5% Bi on carbon (example 1) | 1.40 | 1.3 | 97.5 |
| b | 5% Pd and 3.5% Bi on carbon (example 2) | 1.50 | 1.4 | 97.0 |
| c | 5% Pd and 3.5% Bi on carbon (example 1) | 0.40 | 0.6 | 98.9 |
| d | 5% Pd/C commercially available (DEGUSSA 198 R/W) | 4.40 | 2.6 | 95.1 |

EXAMPLE 5

Preparation of sodium lactobionate by oxidation of lactose.

The operating procedure adopted to carry out this example is identical to the one described in example 4, except for the quantity of raw material implemented which now amounts to 1000 g of solution with 20 wt % of lactose having a purity of 99.8%.

The catalysts used are, on the one hand, the one of example 1 and, on the other hand, a Pd/C catalyst commercially available (DEGUSSA C 101 R/W with 5% Pd).

The numeric data of example 5 are recorded in table II.

TABLE II

| Catalyst used | Reaction time (hr) | Reducing sugars (%) | Lactose conversion rate (%) |
|---|---|---|---|
| 5% Pd and 3.5% Bi on carbon (example 1) | 1.20 | 4.6 | 91 |

In the case of the catalyst commercially available and after four hours' reaction time, the quantity of sodium hydroxide consumed was lower than 10% with respect to the theoretical quantity. Under these conditions, the test was stopped.

EXAMPLE 6

Preparation of polyhydroxycarboxylic acids by oxidation of polysaccharides.

A series of 12 experiments is carried out with, as raw material, eight products resulting from the hydrolysis of starch whose the DE ranges between 90 and 27.7.

The operating procedure adopted for the oxidation of the raw materials identified in table III is thoroughly identical with the one indicated for example 4.

The catalysts are either those according to examples 1 to 3, or the catalyst commercially available used in these examples 1 and 3.

Still according to the same method, there are determined the reaction time and, on the finished product, the percentage of residual reducing sugars which makes it possible to calculate the conversion rate of the polysaccharides.

In table IV, the raw material and the catalyst used have been identified for the twelve experiments and the result of the aforesaid determination has each time been indicated.

TABLE IV

| Raw material | DE | Catalyst | Reaction time (hr) | Reducing sugars (in %) | Conversion rate of the polysaccharides (%) |
|---|---|---|---|---|---|
| Hydrolysate with high DE (e) | 90.0 | Pd/Bi/C according to example 1 | 2.40 | 1.6 | 97.9 |
| Hydrolysate with medium DE (f) | 84.0 | Pd/Bi/C according to example 1 | 2.30 | 6.8* | 97.0 |
| Maltose-rich glucose syrup (g) | 65.8 | Pd/Bi/C according to example 1 | 4.30 | 1.70 | 97.5 |
| Maltose-rich glucose syrup (g) | 65.8 | Pd/Bi/C according to example 2 | 4.20 | 1.80 | 97.2 |
| Maltose-rich glucose syrup (g) | 65.8 | Pd/Bi/C according to example 3 | 4.30 | 1.80 | 97.2 |
| Maltose-rich glucose syrup (g) | 65.8 | Pd/C commercially available | 7.30 | 11.40 | 82.7 |
| Glucose syrup (h) with high DE | 40.8 | Pd/Bi/C according to example 1 | 3.20 | 1.85 | 95.5 |
| Glucose syrup (i) with medium DE | 38.0 | Pd/Bi/C according to example 1 | 2.50 | 1.55 | 96.0 |
| Glucose syrup (i) with medium DE | 38.0 | Pd/C commercially available | 7.45 | 15.0 | 60.0 |
| Glucose syrup (j) with low DE | 33.1 | Pd/Bi/C according to example 1 | 3.00 | 1.70 | 94.9 |
| Glucose syrup (j) with low DE | 40.8 | Pd/Bi/C according to example 3 | 3.05 | 2.50 | 92.5 |
| Maltodextrin (m) with medium DE | 27.7 | Pd/Bi/C according to example 1 | 2.20 | 2.30 | 92.0 |

*fructose content 4.1%

The examination of the results recorded in table IV makes it possible to come to the conclusions developed hereafter.

The catalytic oxidation of the polysaccharides by means of a Pd/Bi or Pd/Pb catalyst on carbon makes it possible to reach a conversion rate of the polysaccharides of 92 to 97% for products whose D.E. value and glucidic distribution range within a very broad field. The oxidation performed with these preferred catalysts is practically total and is not affected by the presence of polysaccharides whose degree of polymerization is higher than 10. The low content of reducing sugars as well as the High Performance Liquid Chromatography (HPLC) indicate that all polysaccharides are oxidized and that the glucidic distribution is integrally preserved.

TABLE III

| Experiment Nr | Definition of the hydrolysate | DE of the hydrolysate | Glucidic spectrum | | | | | | | | | | |
|---|---|---|---|---|---|---|---|---|---|---|---|---|---|
| | | | glucose | maltose | DP3 | DP4 | DP5 | DP6 | DP7 | DP8 | DP9 | DP10–20 | DP20 |
| e | Hydrolysate with high DE | 90 | 85.4 | 9.4 | 3.9 | | | | | 2 | | | |
| f | Hydrolysate with medium DE * | 84 | 71.5 | 14.0 | 4.2 | | | | | 6.1 | | | |
| g | Maltose-rich glucose syrup | 65.8 | 40.2 | 28.3 | 10.2 | 1.6 | 0.8 | 0.8 | 1.2 | 1.7 | 2.4 | 8.7 | 4.0 |
| h | Glucose syrup with high DE | 40.8 | 17.1 | 14.6 | 10.7 | 8.1 | 6.5 | 5.0 | 4.5 | 4.5 | 3.3 | 20.6 | 5.0 |
| i | Glucose syrup with medium DE | 38 | 14.2 | 11.4 | 9.8 | 8.8 | 7.8 | 5.7 | 5.1 | 4.5 | 3.9 | 23.0 | 5.9 |
| j | Glucose syrup with low DE | 33.1 | 11.4 | 9.6 | 8.4 | 7.5 | 6.7 | 5.1 | 4.8 | 4.4 | 4.0 | 27.3 | 10.9 |
| k | Glucose syrup with low content in polysaccharides | 39.8 | 13.1 | 13 | 13 | 7.7 | 10.8 | 11.5 | 2.8 | 2.7 | 2.7 | 17.5 | 4.8 |
| m | Maltodextrine with low DE | 27.7 | 9.3 | 7.7 | 7.7 | 7.8 | 6.6 | 5.9 | 5.1 | 4.7 | 4.2 | 29.2 | 11.2 |

* fructose content 4.1%

In return, the tests carried out with a Pd/C catalyst commercially available indicate that the reaction time as well as the content of reducing sugars significantly increase. The difference is all the more important since the initial D.E. is low. This observation reflects the difficulty in oxidizing polysaccharides whose degree of polymerization is high.

More precisely, in the case of the catalytic oxidation of a glucose syrup having a D.E. of medium value, with a Pd/C non-doped catalyst commercially available, the High Performance Liquid Chromatography (HPLC) shows that only the fraction constituted of glucose is totally oxidized. The maltose fraction is oxidized to approximately 50%, the maltotriose fraction is oxidized to approximately 30% and the upper polysaccharides undergo a minor oxidation only. The Pd/C catalysts commercially available are therefore relatively unsuitable for the total oxidation of the polysaccharides.

We claim:

1. A process for the preparation of polyhydroxycarboxylic acids by way of the selective oxidation of polysaccharides having a reducing terminal function of the aldose type, the said process comprising:
    selecting at least one polysaccharide having a reducing function of the aldose type in the form of an aqueous solution,
    dispersing into the said polysaccharide solution a catalyst based on a noble metal selected from the group consisting of palladium, platinum, rhodium and osmium and fixed on an inert support, said catalyst being "doped" with at least one metal, called promoter and selected from the group consisting of those of the Groups IV, V and VI of the Periodic Table,
    starting the reaction by supplying the polysaccharide solution, having dispersed therein the catalyst, with an oxygen containing gas and with an alkaline agent.

2. Process according to claim 1, wherein the promoter is selected from the group consisting of bismuth, lead, antimony and selenium.

3. Process according to claim 1, wherein the inert support is selected from the group consisting of carbon, alumina, silica, silica-alumina, barium sulfate and titanium oxide.

4. Process according to claim 1, wherein the catalyst is constituted by at least one of the metals of the group consisting of palladium and platinum fixed on carbon and doped by at least one promoter of the group consisting of bismuth and lead.

5. Process according to claim 1, wherein the content in the catalyst of the at least one noble metal of the group consisting of palladium and platinum, expressed in terms of metal, is comprised between 1 and 10 wt % with respect to the support.

6. Process according to claim 1, wherein the content in the catalyst of the at least one metal of the group consisting of bismuth and lead, expressed in terms of metal, is comprised between 1 and 300 wt % with respect to the noble metal.

7. Process according to claim 6, wherein the content in the catalyst of the at least one metal of the group consisting of bismuth and lead, expressed in terms of metal, is comprised between 5 and 10 wt % with respect to the noble metal.

8. Process according to claim 1, wherein the aqueous solution of the at least one polysaccharide comprising a reducing function of the aldose type has a concentration comprised between 5 and 60 wt %.

9. Process according to claim 1, wherein, in the aqueous solution of the at least one polysaccharide, the polysaccharide is selected from the group consisting of starch hydrolysates and glucose syrups, the concentration of the aqueous solution being comprised between 20 and 40 wt %.

10. Process according to claim 1, wherein the temperature at which the reaction of oxidation is carried out, is comprised between 20° and 90° C., the reaction time being comprised between 30 minutes and 5 hours.

11. Process according to claim 10, wherein the temperature to between 25° and 60° C.

12. Process according to claim 1, wherein the pH of the aqueous solution of the at least one polysaccharide wherein is dispersed the catalyst, is maintained by means of at least one alkaline agent at a value comprised between 7.5 and 11.0.

13. Process according to claim 12, wherein the pH of the aqueous solution is between 8.0 and 10.0.

14. A process for the preparation of polyhydroxycarboxylic acids by way of the selective oxidation of polysaccharides having a reducing terminal function of the aldose type from the group consisting of starch hydrolysates and glucose syrups whose D.E. (dextrose equivalent) is comprised between 90 and 5, the said process comprising:
    selecting at least one starch hydrolysate or glucose syrup in the form of an aqueous solution,
    dispersing into the said solution of starch hydrolysate or glucose syrup a catalyst based on a noble metal selected from the group consisting of palladium, platinum, rhodium and osmium and fixed on an inert support, said catalyst being "doped" with at least one metal, called promoter and selected from the group consisting of those of the Groups IV, V and VI of the Periodic Table,
    starting the reaction by supplying the starch hydrolysate or glucose syrup solution, having dispersed therein the catalyst, with an oxygen containing gas and with an alkaline agent.

15. Process according to claim 14, wherein the promoter is selected from the group consisting of bismuth, lead, antimony and selenium.

16. Process according to claim 14, wherein the inert support is selected from the group consisting of carbon, alumina, silica, silica-alumina, barium sulfate and titanium oxide.

17. Process according to claim 14, wherein the catalyst is constituted by at least one of the metals of the group consisting of palladium and platinum fixed on carbon and doped by at least one promoter of the group consisting of bismuth and lead.

18. Process according to claim 14, wherein the content in the catalyst of the at least one noble metal of the group consisting of palladium and platinum, expressed in terms of metal, is comprised between 1 and 10 wt % with respect to the support.

19. Process according to claim 14, wherein the content in the catalyst of the at least one metal of the group consisting of bismuth and lead, expressed in terms of metal, is comprised between 1 and 300 wt % with respect to the noble metal.

20. Process according to claim 19, wherein the content in the catalyst of the at least one metal of the group consisting of bismuth and lead, expressed in terms of metal, is comprised between 5 and 10 wt % with respect to the noble metal.

21. Process according to claim 14, wherein the aqueous solution of the at least one starch hydrolysate and glucose syrup has a concentration comprised between 20 and 40 wt %.

22. Process according to claim 14, wherein the starch hydrolysates and glucose syrups have a D.E. (dextrose equivalent) comprised between 85 and 15.

23. Process according to claim 22, wherein the starch hydrolysates and glucose syrups have a D.E. (dextrose equivalent) comprised between 75 and 15.

24. Process according to claim 14, wherein the amount of catalyst dispersed in the aqueous solution of the at least one starch hydrolysate or glucose syrup is such that the concentration in noble metal of the group consisting of palladium and platinum, expressed in terms of metal, is comprised between 0.005 and 1 wt % with respect to the amount of starch hydrolysate or glucose syrup.

25. Process according to claim 24, wherein the amount of catalyst dispersed in the aqueous solution of the at least one starch hydrolysate or glucose syrup is such that the concentration of noble metal of the group consisting of palladium and platinum, expressed in terms of metal, is comprised between 0.01 and 0.4 wt % with respect to the amount of starch hydrolysate or glucose syrup.

26. Process according to claim 14, wherein the alkaline agent is selected from the group consisting of calcium hydroxide, lithium hydroxide, magnesium hydroxide, zinc carbonate and manganese carbonate.

* * * * *